United States Patent [19]
Laxman

[11] Patent Number: 5,902,893
[45] Date of Patent: May 11, 1999

[54] PURIFICATION OF ORGANOSILANES OF GROUP 13 (IIIA) AND 15 (VA) IMPURITIES

[75] Inventor: Ravi Kumar Laxman, Encinitas, Calif.

[73] Assignee: Air Products and Chemicals, Inc., Allentown, Pa.

[21] Appl. No.: 08/858,800

[22] Filed: May 20, 1997

[51] Int. Cl.$^6$ .................................................. C07F 7/08
[52] U.S. Cl. ............................................................ 556/466
[58] Field of Search ............................................ 556/466

[56] References Cited

U.S. PATENT DOCUMENTS

| | | | |
|---|---|---|---|
| 3,414,603 | 12/1968 | Mlavsky | 556/466 |
| 4,156,689 | 5/1979 | Ashby et al. | 556/466 |
| 4,732,996 | 3/1988 | Moorhead et al. | 556/466 |
| 5,104,999 | 4/1992 | Satoh | 556/466 |
| 5,210,250 | 5/1993 | Watanuki et al. | 556/466 |

OTHER PUBLICATIONS

Hawley's Condensed Chemical Dictionary, 11$^{th}$ ed., N. Irving Sax, et al. (1987).

J. M. Rosamilia, 1994 Proceedings Institute of Environmental Sciences, p. 156.

Advanced Inorganic Chemistry, 5$^{th}$ ed., F. Albert Cotton and Geoffrey Wilkinson, 1988, pp. 162–207.

Amberlite IRA—173 Ion Exchange Resin Separation Technology bulletin, Rohm & Haas (1989).

Robert Kunin and Albert F. Preuss, I&EC Product Research Development, vol. 3., No. 4, (1964), p. 304.

*Primary Examiner*—Paul F. Shaver
*Attorney, Agent, or Firm*—Geoffrey L. Chase

[57] ABSTRACT

A process for removal of Group 13 and/or 15 elements from an organosilane containing Group 13 and/or 15 elements as contaminants comprising contacting the organosilane with a reagent substantially soluble in the organosilane and capable of forming a complex with the Group 13 and/or Group 15 element which is less volatile than the organosilane, wherein the reagent is selected from the group consisting of thiols, alcohols, carboxylic acids, amines or mixtures thereof and separating the organosilane from the complex by distillation.

17 Claims, No Drawings

PURIFICATION OF ORGANOSILANES OF GROUP 13 (IIIA) AND 15 (VA) IMPURITIES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Organosilanes are widely used in the electronics industry. For example, tetraethylorthosilicate (TEOS) is used as a major source for depositing silicon dioxide. Group 13 (IIIA) and 15 (VA) elements behave as impurities in obtaining silicon dioxide films. One of the challenges for the industry involves removal of impurities effectively from TEOS to make ultrahigh purity TEOS (see Hawley's Condensed Chemical Dictionary, 11th ed., N. Irving Sax, et al. (1987) for the current numbering in the Periodic Table of the Elements).

J. M. Rosamilia, 1994 Proceedings Institute of Environmental Sciences, pp156 demonstrate some of the methods of analysis and impurity levels in TEOS. They also describe the difficulty in removing boron impurities because it forms volatile triethoxyboron complex which distills along with TEOS.

Ultra high purity precursors are extremely important for the fabrication of high performance devices in the semiconductor industry. As the device density increases with the number of transistors, the dimensions of the device decrease to submicroscopic features. At 0.25 µm technology and beyond, even very low levels of impurities (ppb to parts per trillion) effect the device in high failure rates and low performance.

In addition to the miniaturization and design of multilevels, the thickness of the dielectric layers between the levels is continuously reduced. This reduction in thickness of the dielectric layers is required for devices to operate at high speeds in the gigahertz regime. As a result even small amounts of impurities diffuse readily at high temperatures through these dielectric layers and cause device failures. In the case of boron and phosphorus impurities, this effect is dramatic at high process temperatures. This is because light atoms, such as boron ($B^{11}$) impurities, easily diffuse through shallow junctions.

Some of the other problems which are caused by the presence of impurities are:
1) Leakage current at junctions.
2) Unstable electrical characteristics of silicon dioxide.
3) Localized eutectic points with silicon o form undesirable alloys.

Highly sensitive techniques are routinely utilized in analyzing all the materials. Instrumentation such as atomic pressure ionization mass spectroscopy (APIMS) Inductively coupled plasma mass spectrometer (ICPMS) and Inductively coupled plasma atomic emission (ICPAE) are used to detect low levels of impurities in the range of <5 ppb.

Typical reactions that can be expected with boron are described in Advanced Inorganic Chemistry, 5th ed., F. Albert Cotton and Geoffrey Wilkinson, 1988, pp. 162–207.

Removal of boron and other impurities in water was earlier demonstrated by use of a boron specific resin (Amberlite IRA-173 Ion Exchange Resin Separation Technology bulletin, Rohm & Haas (1989). Ion exchange resins which contain N-methylglucamine have been used specifically to bind boron as boric acid. This technique has been used in removing boron from irrigation waters and solutions, see Robert Kunin and Albert F. Preuss, I&EC Product Research Development, Vol 3., No 4., (1964). pp 304.

High purity alkoxysilanes have been purified by using chelating resins such as Chitosan followed by vacuum distillation and diffusion with inert gases. The chelating resin contained groups such as $HN(CH_2COOH)_2$, see Japanese Patent JP 04082892 A2 920316 (1990). Here, they demonstrate removal of impurities such as Na, K, Ca and Cu.

Typically, TEOS is manufactured using ultra high purity starting materials to minimize contaminants. Chlorine, sodium and potassium are some of the common impurities. Halides were removed in alkoxysilanes by reacting with zinc metal to provide purified alkoxysilanes, see U.S. Pat. No. 5,104,999.

The synthesis and manufacture of TEOS for the semiconductor industry is carefully monitored by using high purity silicon containing starting materials and impurity free reagents. The product thus obtained is further purified by fractional distillation. These fractional distillations result in loss of yield in the form of prefractions (25–30%). Even after several repeated distillations TEOS may still contain contamination above 50 ppb.

The prior art generally involves use of ion exchange resins to reduce Group 13 impurities. Other techniques involve separation of boron impurities from aqueous media and purification of alkoxysilanes involved repeated fractional distillation and use of high purity starting materials.

The present invention overcomes the deficiencies in the prior art purification of organosilanes of Group 13 and 15 impurities by providing a technique for producing high purity products using reagents soluble in the product which are less volatile than the product. This results in decreased distillation losses and higher purities, as described in greater detail below.

BRIEF SUMMARY OF THE INVENTION

The present invention is a process for removal of Group 13 and/or 15 impurities from an organosilane containing Group 13 and/or Group 15 elements, comprising contacting an organosilane selected from the group consisting of:
i) $X_{4-n}SiY_n$
  where n=0–4;
  when n=0, $X=R^1$;
  when n=1–2, $Y=R^2$ and X=H, F or $R^1$;
  when n=3–4, $Y=OR^2$ and X=H, F or $R^1$;
  where $R^1$ and $R^2$ are independently alkyl, alkenyl, alkynyl or aryl radicals or mixtures thereof; or
ii) cyclical $[-(R^1)(R^2)SiO-]_m$
  where m=3–6, and $R^1$ and $R^2$ are independently H, F, alkyl, alkenyl, alkynyl or aryl radicals or mixtures thereof; or
iii) $(R^1)_3SiO-[(R^1)(R^2)SiO-]_mSi(R^2)_3$
  where m=0–4;
  where $R^1$ and $R^2$ are independently H, F, alkyl, alkenyl, alkynyl or aryl radicals or mixtures thereof;
and mixtures of i), ii) or iii) thereof, with a reagent substantially soluble in the organosilane and forming a complex with the Group 13 and/or Group 15 element which is less volatile than the organosilane. The reagent is selected from an organic molecule consisting of any of the following functionalities: thiols, alcohols, carboxylic acids, amines or mixtures thereof. The complex thus formed by the reagent is separated from the organosilane by distillation.

Preferably, the Group 13 and/or Group 15 element is selected from the group consisting of boron, aluminum, gallium, indium, thallium, phosphorus, arsenic, antimony, and bismuth and mixtures thereof.

Preferably, the reagent is selected from the group consisting of an alcohol, a carboxylic acid or mixtures thereof, wherein the reagent has a $pK_a$ in the range of 3 to 19.7, preferably 9 to 11, most preferably approximately 10.

Alternatively, the reagent is selected from the group consisting of primary, secondary, tertiary amines or mixtures thereof.

Preferably, the reagent is added in an amount in the range of approximately 3 to 10 mole equivalents of the Group 13 and/or Group 15 element to be removed.

Alternatively, the reagent is added in an amount in at least 10% of a stoichiometric excess for the Group 13 and/or Group 15 element to be removed.

The present invention is more specifically a process for removal of an element selected from the group consisting of boron, phosphorus and mixtures thereof from an tetraalkoxysilane containing the element as a contaminant comprising contacting the tetraalkoxysilane with a reagent selected from the group consisting of 2,4,6-trimethylphenol, triphenylsilanol, dodecanol and mixtures thereof to form a complex with the element and separating the tetraalkoxysilane from the complex by distillation.

The present invention is most specifically a process for removal of an element selected from the group consisting of boron, phosphorus and mixtures thereof from tetraethoxysilane containing the element as a contaminant comprising contacting the tetraethoxysilane with 2,4,6-trimethylphenol to form a complex with the element and separating the tetraethoxysilane from the complex by distillation.

BRIEF DESCRIPTION OF THE SEVERAL VIEWS OF THE DRAWINGS

Not Applicable

DETAILED DESCRIPTION OF THE INVENTION

The present invention involves removal of Group 13 and/or 15 impurities to low levels, such as 5 parts per billion by weight (ppb) or less, from organosilanes, such as tetraethylorthosilicate also known as tetraethoxysilane (TEOS). The present invention uses sterically bulky alcohol, carboxylic acid and amine reagents in a novel approach to trap impurities selectively without changing any of the current industry distillation methods for the purification of organosilanes, such as alkoxysilanes, specifically TEOS.

The reagent complexes with volatile impurities specifically to form low or non-volatile complexes for easy separation during a fractional distillation process. For example, in the case of TEOS, the reagent specifically binds to impurities to form low or non-volatile complexes, and can be removed as undistilled residual heals. This method allows one to retain the high purity of TEOS (>99.9999% by weight based on metal assay) without altering the fractional distillation processes and allows higher yields of the product effectively. The resulting product has less than <5 ppb by weight of Group 13 and/or 15 impurities and results in at least 99% by volume removal of the impurity.

Small amounts of boron can exist in TEOS both as inorganic boron and organic boron. Due to the large concentration of TEOS, it is envisaged that boron rapidly exchanges with ethoxy groups in the TEOS and readily forms triethoxyboron. Triethoxyboron has a relatively high vapor pressure and can easily distill with TEOS during a distillation purification process. The reagent which is used in the present invention's purification process coordinates and encapsulates the boron coordination sphere, such that the exchange process with ethoxy groups in the TEOS is substantially retarded. The resulting boron complex is a non-volatile complex which cannot be easily distilled as an overhead or light fraction under the traditional conditions of TEOS purification. The coordination process of the reagent with boron is depicted below:

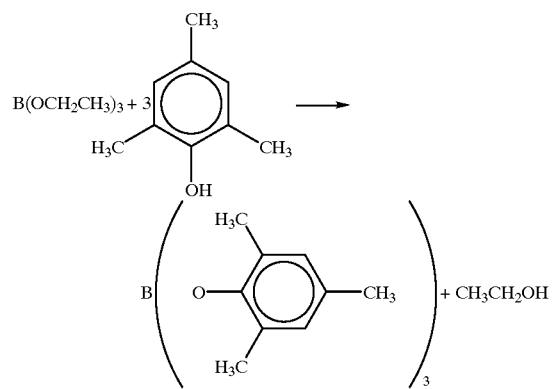

The important aspect of the present invention is that the reagent enhances distillation by creating greater disparity in the volatility of the complexed Group 13 and/or 15 impurity and the product. Relevant volatility values are set forth below:

| Chemical | Vapor pressure (Torr) |
|---|---|
| TEOS | 1.3 at 20 C. |
| Triethylborate | 11 at 20 C. |
| Triethylphosphate | 1.0 at 39 C. |

Reagent 2,4,6-trimethylphenol volatility is much lower than 1.3 Torr at 20 C and the volatility of the reagent is near the detection limits of analytical equipment. The resulting complex $B(OC_9H_{11})_3$ volatility will also be negligible at 20° C.

Traditionally, to obtain high purity TEOS, large prefractions (25–30%) were required to remove boron and other impurities completely. In addition to the reduction of boron impurities to <5 ppb, it is important to minimize prefraction losses effectively. The present invention focuses on removal of boron and phosphorus impurities in organosilanes. This method involves addition of a complexing agent to an organosilane sample prior to distillation.

Although not wanting to be held to any particular theory the present inventor believes that acidic alcohols, such as phenols, easily dissociate to give phenoxides and acidic protons. Under these conditions boron alkoxides undergo facile acid catalyzed ligand exchange with the phenoxide ions to form non-volatile complexes. These non-volatile complexes or ligands of the impurities are easily retained in the heals of the distillation for easy separation.

The following organic reagents can be used for removing Group 13 and Group 15 impurities in the purification of organosilicon compounds.

a) Mono or polyhydric alcohols (—OH) and thiols (—SH), such as R—OH and R—SH, where R=organic group $C_1$–$C_{20}$; preferably $C_1$–$C_{10}$;

b) Carboxylic acids (—COOH), such as RCOOH, where R=organic group $C_1$–$C_{20}$; preferably $C_1$–$C_{10}$;

c) Primary, secondary and tertiary amines (—NRR'R") containing the group, where R, R', R" individually=H or an organic group $C_1$–$C_{20}$; preferably $C_1$–$C_{10}$, but at least one R group must be an organic group;

d) A combination of any of the above groups as listed in a–c.

| Class | $p^{Ka}$ |
|---|---|
| Carboxylic acids | |
| RCOOH | 3–5 |
| e.g.: $C_6H_3R^1R^2R^3O_2$ | 3 |
| Alcohols | |
| R—OH | 15–19.7 |
| e.g.: $C_6H_3R^1R^2R^3O$ | 7–10.8 |
| Thiols | |
| R—SH | 7.8–16 |
| e.g.: $C_6H_3R^1R^2R^3S$ | 7.8–10 |
| Amines | |
| $R_2$—NH | 7–11 |
| e.g.: $C_6H_3R^1R^2R^3N$ | 7–8 | a) R = $C_1$–$C_{20}$; preferably $C_1$–$C_{10}$ hydrocarbon
b) $R^1R^2R^3$ = are individually H or $C_1$–$C_{20}$; preferably $C_1$–$C_{10}$ hydrocarbons, but $R^1 + R^2 + R^3$ is no greater than $C_{14}$; preferably $C_4$.

The preferred reagent would be a organic ligand which can form non-volatile complexes with the impurities. In such cases, bulky organic groups provide better reagents by increasing the boiling points of the reagents and also the resulting complexes. The organic groups can be alkyl, alkenyl, aryl with the number of carbons in the range of $C_1$–$C_{20}$; preferably $C_1$–$C_{10}$.

More specifically: bulky organic acids and alcohols with hydrogen ionization potentials or $pK_a$'s in the range of 3–19.7, preferrably 9–11, most preferably approximately 10, which form non-volatile complexes with Group 13 and Group 15 impurities are contemplated.

More specifically: substituted phenols and alkylalcohols have been used as successful reagents in removing Group 13 and Group 15 impurities. Organic reagents which can be used for purification of organosilicon compounds by removing Group 13 and Group 15 impurities typically have $pK_a$ values in the range of 3–19.7.

The reagent should be substantially soluble to form an essentially homogeneous solution so that it can getter the impurities in TEOS, and it should be less volatile than the organosilane prior to complexing or coordinating with the Group 13 and/or 15 element.

Typically stoichiometrically three to ten mole equivalents of the reagent should be used, but in some circumstances to ensure complete reaction of the Group 13 and/or 15 element with the reagent an excess amount (10%) of reagent is appropriate.

The determination of the amount of reagent to use in the range of 3 to 10 mole equivalents or 10% excess is set forth below:

$$\frac{\text{Initial Boron Concentration } (ppb) \text{ per Kilogram}}{\text{Mol. Wt. of Borons (gms)}} \times$$

$$3 \times \text{Mol. Wt. of reagent} = \text{gms of reagent required}$$

Exemplary preferred reagents are phenols with $C_1$ to $C_3$ alkyl groups, such as 2,4,6-trimethylphenol, 2,6-dimethylphenol, and 2,6-diisopropylphenol.

The advantages of the method of the present invention for purification of organosilanes are:

1) No pretreatment is required to remove large amounts of Group 13 and/or 15 impurities.
2) The distillation parameters to obtain high purity organosilanes are not changed.
3) The Group 13 and/or 15 contamination may be reduced to <5 ppb.
4) No major prefractions are necessary.
5) Minimizes waste disposal of prefractions.
6) The impurities are concentrated in the heals and can be easily removed after distillation processes.
7) Economical for organosilane manufacturing, such as TEOS.

The organosilanes which are contemplated for the present invention are selected from the group consisting of:

i) $X_{4-n}SiY_n$
   where n=0–4;
   when n=0, $X=R^1$;
   when n=1–2, $Y=R^2$ and X=H, F or $R^1$;
   when n=3–4, $Y=OR^2$ and X=H, F or $R^1$;
   where $R^1$ and $R^2$ are independently alkyl, alkenyl, alkynyl or aryl radicals or mixtures thereof; or ii) cyclical $[—(R^1)(R^2)SiO—]_m$
   where m=3–6, and $R^1$ and $R^2$ are independently H, F, alkyl, alkenyl, alkynyl or aryl radicals or mixtures thereof;

iii) $(R^1)_3SiO—[(R^1)(R^2)SiO—]_mSi(R^2)_3$
   where m=0–4;
   where $R^1$ and $R^2$ are independently H, F, alkyl, alkenyl, alkynyl or aryl radicals or mixtures thereof;
   and mixtures of i), ii), or iii) thereof.

Specific compounds contemplated in each group include:
1) Alkyl silanes: Di, Tri and Tetraalkylsilanes; e.g Diethylsilane, Triethylsilane and Tetraethylsilane.
2) Alkoxysilanes: Trialkoxysilane, Flurotrialkoxysilane and tetraalkoxysilane; e.g Triethoxysilane, Florotriethoxysilane, Tetraethoxysilane and Tetramethoxysilane.
3) Cyclicalkoxysilanes: Tetraalkylcyclotetrasiloxane and Octaalkylcyclotetrasiloxane; e.g Tetramethylcyclotetrasiloxane, Tetraethylcyclotetrasiloxane, Octamethylcyclotetrasiloxane and Octaethylcyclotetrasiloxane.
4) Silicones, Alkyldisiloxane and Alkoxydisiloxanes: Trialkyldisiloxane, Tetraalkyldisiloxane, and Hexaalkyldisiloxane, Trialkoxydisiloxane, Tetraalkoxydisiloxane, hexaalkoxydisiloxane; e.g Trimethyldisiloxane, Tetramethyldisiloxane, Hexamethyldisiloxane, Triethyldisiloxane, Tetrethyldisiloxane, Hexaethyldisiloxane, Octamethyltrisiloxane, Decamethyltetrasiloxane, 1,1,1,3,5,5,5-heptamethyltrisiloxane, 1,1,3,5,5-pentamethyl-1,3,5-triphenyltrisiloxane and polymeric silicone oils.

The Group 13 and/or Group 15 element contemplated for removal in the present invention are selected from the group consisting of boron, aluminum, gallium, indium, thallium, phosphorus, arsenic, antimony and bismuth and mixtures thereof.

Several comparative examples were run which represent organosilane or TEOS processing exemplary of the prior art for purification of Group 13 and/or 15 impurities such as boron and phosphorus.

COMPARATIVE EXAMPLE 1

In water purification processes, water is passed over an Amberlite resin to remove traces of boron. A similar process was attempted by passing TEOS which contained boron (a range of 600–1000 ppb) and phosphorus (>10 ppb) over Amberlite IRA 173. The purified TEOS was analyzed by ICPAE for boron and phosphorus. The analysis indicated inconsistent data with no significant improvement in impurity reduction (boron levels remained in the range of 100–750 ppb and phosphorus >10 ppb) when compared to a blank fractional distillation.

This process is not effective for purification of production quantities of organosilicon compounds for two main reasons. First, the reduction is not nearly as quantitative and secondly, it is a less economical process both in terms of the large quantities of resin required and disposal of waste resin.

COMPARATIVE EXAMPLE 2

The main ingredient in Amberlite IRA-173 is N-methyl glucamine. A comparative distillation for the purification for boron and phosphorus was carried out using a large excess of N-methylglucamine as a reagent as described in Comparative Example 1. The distilled product gave an analysis of boron and phosphorus in the range of 140–300 ppb. These results were similar to a blank run (Table 1, below) and indicate that there was no significant improvement.

Initial experiments to complex boron in TEOS as a non-volatile boron complex using the technique of the present invention were attempted using several alcohols, such as; glycerol, 1-dodecanol, triphenylsilanol and 2,4,6 trimethylphenol. These experiments gave results with decreasing amounts of impurities in the distilled product. The best results were obtained when 2,4,6 trimethylphenol was used as the reagent, see Table 1, below. As a result, a combination of sterically bulky and acidic alcohols are envisaged as appropriate choices for gettering the impurities effectively. The resulting complexes with these alcohol form non-volatile complexes at these distillation temperatures and can be retained in the heals of the distillation for easy separation.

In contrast to the above comparative examples of the prior art, the following examples demonstrate the unexpected enhancement in purification that the technique of the present invention provides. In each example, the fractional distillation of TEOS was carried out using an oldershaw column. The TEOS in the reboiler was heated to its boiling temperature (168.9° C.) at atmospheric pressure. To form a non-volatile boron complex in a TEOS sample with predetermined amount of boron contamination, typically stoichiometrically three mole equivalents of the reagent were used, but in some examples as noted below to ensure complete reaction of the boron with the reagent an excess amount (10%) of reagent was used.

EXAMPLE 3

3 kgs of crude TEOS which contains 770 ppb boron as determined by ICPAE analysis was fractionally distilled without being treated with a reagent to complex with the boron for comparison purposes with examples that used such reagents (Blank). The fractional distillation of TEOS was carried out using an oldershaw column. The reboiler was heated to the boiling temperature of TEOS (168.9° C.) at atmospheric pressure. After an initial prefraction of 100 mls (3%) pure TEOS was collected under an nitrogen atmosphere. The TEOS was then analyzed by GC/MS, GC assay, and ICPAE. The analysis of the purified sample indicated boron concentration in the range of 243 ppb. This analysis is indicative of 68% boron removal. The results are reported in Table 1, below.

EXAMPLE 4

3 kgs of crude TEOS which contains 3000 ppb boron as determined by ICPAE analysis was treated with a large excess of 2,4,6 trimethylphenol. The fractional distillation of TEOS was carried out using an oldershaw column. The reboiler was heated to the boiling temperature of TEOS (168.9° C.) at atmospheric pressure. After an initial prefraction of 100 mls (3%) pure TEOS was collected under an nitrogen atmosphere. The TEOS was then analyzed by GC/MS, GC assay, and ICPAE. The analysis of the purified sample indicated boron and phosphorus concentration in the range of 1–5 ppb. This analysis is indicative of >99% boron removal. The purity of TEOS was determined to be >99.9999% based on metal assay.

EXAMPLE 5

3 Kgs of crude TEOS which contains 769 ppb of boron as determined by ICPAE analysis was treated with 3 mole equivalents of 2,4,6 trimethylphenol. The distillation was carried out as described in Example 4. The TEOS was then analyzed by GC/MS, GC assay, and ICPAE. The analysis of the purified sample indicated boron and phosphorus concentration in the range of <5 ppb. This analysis is indicative of >99% boron removal. The purity of TEOS was determined to be >99.9999% based on metal assay.

EXAMPLE 6

3 Kgs of crude TEOS with a predetermined amount of boron (3000 ppb) is allowed to react with excess of 1-dodecanol as described in Example 4. The product was then analyzed by GC/MS, GC assay, and ICPAE. The purified product indicated boron and phosphorus concentration in the range of <300 ppb. This analysis is indicative of >95% boron removal. The results are listed in Table 1, below.

EXAMPLE 7

3 Kgs of crude TEOS with a predetermined amount of boron (770 ppb) is allowed to react with a large excess of triphenylsilanol as described in Example 4. The product was then analyzed by GC/MS, GC assay, and ICPAE. The purified product indicated boron and phosphorus concentration at <76 ppb. This analysis is indicative of >90% boron removal. The results are listed in Table 1, below.

TABLE 1

| REAGENT | INITIAL BORON (ppb) | FINAL BORON (ppb) | % REMOVED |
| --- | --- | --- | --- |
| No Reagent Blank* | 770 | 243 | 68 |
| Glycerol | 625 | 80 | 87 |
| Dodecanol | 3000 | 300 | 95 |
| Triphenylsilanol | 770 | 76 | 90 |
| 2,4,6-trimethylphenol | 769 | 5 | 99 |
| 2,4,6-trimethylphenol | 3000 | 5 | 99 |

*A blank fractional distillation is carried out without adding a reagent.

These results indicate that impurities are effectively removed when either a stoichiometric or an excess amount of the reagents of the present invention are used. To completely complex boron in a TEOS sample with a predetermined amount of boron contamination, stoichiometrically three mole equivalents of the reagent are sufficient. A range of 3–10 mole equivalents of the reagent can be used. However, to ensure complete reaction of the boron with the reagent an excess of 10% is recommended.

Organosilicon compounds, such as tetraethylorthosilicate, are purified using this method. Other compounds which can be purified using this method include; alkylsilanes, alkoxysilanes, cyclialkyloxysilanes and alkyldisiloxanes and alkoxydisiloxanes as recited above.

The electronics industry demands ever increasing purities in the precursor chemicals used to fabricate semiconductor materials and devices. Organosilanes, such as TEOS, constitute a significant precursor for that industry in forming silicon dioxide layers and devices. As the line width and device geometries shrink, contaminants become more critical to semiconductor device fabrication and impurities must be minimized for high yields of semiconductor devices.

The present invention allows precursor organosilanes to the electronics industry to meet the increasing purity requirements imposed by large scale integrated circuit designs using the same fractional distillation purification process and equipment traditionally used in the industry, while achieving unexpected reductions in Group 13 and/or 15 impurities with simple, inexpensive reagents which are substantially soluble with the organosilane and which form low volatility complexes with the impurities to facilitate their removal during the traditional fractional distillation purification.

The significantly enhanced purity levels with little additional capital, raw material or power expense of the present invention is a significant improvement in precursor supply to the electronics industry. Additionally, due to the enhanced differential volatility of the organosilane product from the Group 13 and/or 15 element impurity complexed with the present inventions reagents, losses of organosilane in the distillation process are reduced, resulting in increased yields of product and less environmental waste of fractionation cuts.

The present invention has been set forth with regard to several preferred examples, but the full scope of the present invention should be ascertained from the claims which follow.

I claim:

1. A process for removal of Group 13 and/or 15 elements from an organosilane containing Group 13 and/or 15 elements as contaminants comprising contacting said organosilane selected from the group consisting of:

i) $X_{4-n}SiY_n$ where n=0–4;

when n=0, $X=R^1$;

when n=1–2, $Y=R^2$ and X=H, F or $R^1$;

when n=3–4, $Y=OR^2$ and X=H, F or $R^1$;

where $R^1$ and $R^2$ are independently alkyl, alkenyl, alkynyl or aryl radicals or mixtures thereof; or ii) cyclical $[-(R^1)(R^2)SiO-]_m$ where m=3–6, and $R^1$ and $R^2$ are independently H, F, alkyl, alkenyl, alkynyl or aryl radicals or mixtures thereof; or iii) $(R^1)_3SiO-[(R^1)(R^2)SiO-]_mSi(R^2)_3$ where m=0–4;

where $R^1$ and $R^2$ are independently H, F, alkyl, alkenyl, alkynyl or aryl radicals or mixtures thereof;

and mixtures of i), ii) or iii) thereof, with a reagent substantially soluble in said organosilane and capable of forming a complex with said Group 13 and/or Group 15 element which is less volatile than said organosilane, wherein said reagent is selected from the group consisting of thiols, alcohols, carboxylic acids, amines or mixtures thereof, forming said complex and separating said organosilane from said complex by distillation.

2. The process of claim 1 wherein said organosilane is a tetraalkoxysilane.

3. The process of claim 1 wherein said Group 13 and/or Group 15 element is selected from the group consisting of boron, aluminum, gallium, indium, thallium, phosphorus, arsenic, antimony and bismuth and mixtures thereof.

4. The process of claim 1 wherein said organosilane is a trialkoxysilane.

5. The process of claim 1 wherein said reagent is selected from the group consisting of an alcohol, a carboxylic acid or mixtures thereof, wherein said reagent has a $pK_a$ in the range of 3 to 19.7.

6. The process of claim 1 wherein said reagent is an alcohol wherein said reagent has a $pK_a$ in the range of 9 to 11.

7. The process of claim 1 wherein said reagent is selected from the group consisting of primary, secondary, tertiary amines or mixtures thereof.

8. The process of claim 7 wherein said reagent has a $pK_a$ in the range of 3 to 19.7.

9. The process of claim 1 wherein said reagent is added in an amount in the range of approximately 3 to 10 mole equivalents of the Group 13 and/or Group 15 element to be removed.

10. The process of claim 1 wherein said reagent is added in an amount in at least 10% of a stoichiometric excess for the Group 13 and/or Group 15 element to be removed.

11. The process of claim 1 wherein said element is removed from said organosilane in an amount of at least 99% by weight.

12. The process of claim 1 wherein said element is removed from said organosilane in an amount of no greater than 5 ppb by weight of the element in the organosilane.

13. The process of claim 1 wherein said reagent has an organic functionality of $C_1$ to $C_{20}$.

14. The process of claim 1 wherein said reagent has an organic functionality of $C_1$ to $C_{10}$.

15. The process of claim 1 wherein said reagent is substantially less volatile than said organosilane.

16. A process for removal of an element selected from the group consisting of boron, phosphorus and mixtures thereof from a tetraalkoxysilane containing said element as a contaminant comprising contacting said tetraalkoxysilane with a reagent selected from the group consisting of 2,4,6-trimethylphenol, triphenylsilanol, dodecanol and mixtures thereof to form a complex with said element and separating said tetraalkoxysilane from said complex by distillation.

17. A process for removal of an element selected from the group consisting of boron, phosphorus and mixtures thereof from tetraethoxysilane containing said element as a contaminant comprising contacting said tetraethoxysilane with 2,4,6-trimethylphenol to form a complex with said element and separating said tetraethoxysilane from said complex by distillation.

* * * * *